United States Patent [19]
Nicolau et al.

[11] Patent Number: 6,034,030
[45] Date of Patent: Mar. 7, 2000

[54] VINYL ACETATE CATALYST PREPARATION METHOD

[75] Inventors: Ioan Nicolau; Philip M. Colling; Leland R. Johnson, all of Corpus Christi, Tex.; Michael A. Loewenstein, Solon, Ohio

[73] Assignee: Celanese International Corporation, Dallas, Tex.

[21] Appl. No.: 09/026,644

[22] Filed: Feb. 20, 1998

Related U.S. Application Data

[63] Continuation-in-part of application No. 08/823,592, Mar. 25, 1997, abandoned, which is a continuation of application No. 08/489,541, Jun. 12, 1995, abandoned, which is a continuation-in-part of application No. 08/200,137, Feb. 22, 1994, abandoned.

[51] Int. Cl.[7] ................................................. B01J 23/44
[52] U.S. Cl. ........................ 502/326; 502/333; 502/334; 502/330; 502/344
[58] Field of Search ..................................... 502/333, 334, 502/330, 243, 261, 262, 344, 326

[56] References Cited

U.S. PATENT DOCUMENTS

| | | | |
|---|---|---|---|
| 3,775,342 | 11/1973 | Kronig et al. | 252/430 |
| 3,822,308 | 7/1974 | Kronig et al. | 260/497 |
| 4,048,096 | 9/1977 | Bissot | 252/430 |
| 4,087,622 | 5/1978 | Nakamura et al. | 560/245 |
| 4,490,481 | 12/1984 | Boitiaux et al. | 502/330 |
| 5,274,181 | 12/1993 | Bartley et al. | 560/245 |
| 5,314,858 | 5/1994 | Colling | 502/330 |
| 5,332,710 | 7/1994 | Nicolau et al. | 502/243 |
| 5,691,267 | 11/1997 | Nicolau et al. | 502/330 |
| 5,948,724 | 9/1999 | Nicolau et al. | 502/331 |

FOREIGN PATENT DOCUMENTS 1 521 652   8/1978   United Kingdom .

*Primary Examiner*—Thomas Dunn
*Assistant Examiner*—Christina Ildebrando
*Attorney, Agent, or Firm*—M. Susan Spiering

[57] ABSTRACT

A method is provided to manufacture a palladium-gold catalyst by separately impregnating and fixing the palladium and gold and reducing the fixed solids to free metal on a suitable support useful for vinyl acetate manufacture from ethylene and acetic acid.

11 Claims, No Drawings

VINYL ACETATE CATALYST PREPARATION METHOD

RELATIONSHIP TO PRIOR APPLICATIONS

This application is a continuation in part of U.S. Ser. No. 08/823,592, filed Mar. 25, 1997, now abandoned, which is a continuation of U.S. Ser. No. 08/489,541 filed Jun. 12, 1995, abandoned, which is a continuation in part of U.S. Ser. No. 08/200,137, filed on Feb. 22, 1994, abandoned.

BACKGROUND OF THE INVENTION

1. Field of the Invention

The present invention relates to a novel method of producing a catalyst useful in the reaction of ethylene, oxygen and acetic acid in the vapor phase to form vinyl acetate. In particular, the present invention is directed to a novel method of forming a catalyst useful in the catalytic formation of vinyl acetate in which said catalyst comprises metallic palladium and gold deposited on a suitable porous support.

2. Description of the Prior Art

It is known in the art that vinyl acetate can be produced by reacting ethylene, oxygen, and acetic acid in the gaseous phase and in the presence of a catalyst comprising palladium, gold and an alkali metal acetate supported on certain carrier materials such as silica. Generally, such catalyst system exhibits a high activity. Unfortunately, results utilizing such palladium and gold catalysts have been inconsistent. This inconsistency appears to be based somewhat on the distribution pattern or profile of the catalyst components which are deposited on and in relation to the support. For example, when use is made of the known vinyl acetate catalyst systems comprising a porous support with palladium and gold, the metal components deposited at or about the support interiors or central regions do not contribute significantly to the reaction mechanism, since the reactants are not readily able to diffuse into the central or inner regions of the porous network of the catalyst. Hence, the reaction occurs substantially only at the outermost or surface regions of the catalyst. The catalyst components in the interior regions of the support do not largely contribute to the reaction scheme, resulting in a reduction in catalytic efficiency per unit weight of the catalyst components. Furthermore, the use of a highly active catalyst at times gives rise to side reactions and, therefore, leads to a reduced selectivity to vinyl acetate.

Various patents have been granted based on the desire to more evenly distribute and anchor the gold and palladium catalytic components within a narrow band on the support surface to provide a vinyl acetate catalyst having high yield, good selectivity and long life. Examples of such patents include U.S. Pat. Nos. 5,274,181; 4,087,622; 4,048,096; 3,822,308; 3,775,342 and British Patent 1,521,652. Certain U.S. patents assigned to Hoechst Celanese Corporation, U.S. Pat. Nos. 5,314,858 and 5,332,710 and their PCT and foreign counterparts disclose and claim improvements in the basic technology.

The basic method of forming the vinyl acetate catalyst containing palladium and gold deposited on a catalyst support comprises (1) impregnating the support with aqueous solutions of water-soluble palladium and gold compounds, (2) precipitating water-insoluble palladium and gold compounds on the catalyst support by contacting the impregnated catalyst support with a solution of compounds capable of reacting with the water-soluble palladium and gold compounds to form the insoluble precious metal compounds (3) washing the treated catalyst with water to remove anions which are freed from the initially impregnated palladium and gold compounds during precipitation and (4) converting the water-insoluble palladium and gold compounds to the free metal by treatment with a reducing agent. A final treatment usually involves (5) impregnating the reduced catalyst with an aqueous alkali metal acetate solution and (6) drying the final catalyst product.

Prior art attempts to provide a uniform distribution of the palladium and gold metals on the support has involved some manipulation of the above mentioned steps and/or by using support materials having various specified pore dimensions.

U.S. Pat. No. 5,314,858, pertains to a method for (1) simultaneously or successively impregnating a catalyst support with aqueous solutions of palladium and gold salts such as sodium-palladium chloride and auric chloride, (2) fixing the precious metals on the support by precipitating water-insoluble palladium and gold compounds by treatment of the impregnated supports with a reactive basic solution such as aqueous sodium hydroxide which reacts to form hydroxides of palladium and gold on the support surface, (3) washing with water to remove the chloride ion (or other anion), and (4) reducing the precious metal hydroxides to free palladium and gold, wherein the improvement comprises during fixing step (2) utilizing two separate precipitation steps wherein the amounts of the reactive compound in contact with the salt-impregnated support in each step is no more than that required to react with the water soluble precious metal compounds impregnated in the support. Between the separate fixing or precipitation steps, the support which has been impregnated with the reactive basic solution is allowed to stand for a set period of time to allow precipitation of the water insoluble precious metal compounds before the second fixing step in which additional reactive basic compound is added to the support.

It is an object of the present invention to provide a method of preparing a vinyl acetate catalyst which contains palladium and gold on a porous support in which the fixing of the water soluble precious metal compounds as water insoluble compounds on the support can be achieved by contacting the impregnated support with sufficient reactive compound to insure complete precipitation and fixing of the precious metal compounds onto the support in multiple fixing steps.

SUMMARY OF THE INVENTION

It has now been found that particularly active supported catalysts containing palladium and gold useful for the production of vinyl esters from ethylene, lower carboxylic acids with 24 carbon atoms and oxygen in the gas phase at elevated temperature and at normal or elevated pressure can be obtained by modifying steps (1) and (2) of the process as described above. Typically, during the precipitation step (2), the impregnated catalyst support has been impregnated with one or more solutions of the reactive compound and the oxide (hydroxide) of both is caused to precipitate simultaneously for such time as is necessary to complete precipitation of the insoluble precious metal compounds. During a typical precipitation according to the prior art we have noticed that the palladium precipitates at a faster rate than gold precipitates and incremental amounts of unprecipitated gold can leach from the catalyst support prior to its being immobilized by precipitation or in a subsequent washing step. This is a cause for the palladium to gold ratio to vary from impregnation to precipitation. Although the problem exists with precipitant solutions equal to the pore volume of the support, an even more serious problem exists when precipitation is carried out by immersing the impregnated supports in dilute precipitants.

To overcome this problem and in accordance with the present invention, a useful catalyst is formed by (1) non-successively impregnating a catalyst support with aqueous solutions of palladium and gold salts such as sodium-palladium chloride and auric chloride, (2) non-successively fixing each of the precious metals on the support by pre-cipitating water-insoluble palladium and gold compounds by treatment of the impregnated supports with a reactive basic solution such as aqueous sodium hydroxide which reacts to form hydroxides of palladium and gold on the support surface, (3) washing with water to remove the chloride ion (or other anion), and (4) reducing the precious metal hydroxides to free palladium and gold.

DETAILED DESCRIPTION OF THE INVENTION

In the preparation of the improved catalyst of the present invention, a suitable catalyst support is first impregnated with an aqueous solution containing either a water-soluble palladium compound or a water soluble gold compound. Palladium (II) chloride, sodium palladium (II) chloride and palladium (II) nitrate are examples of suitable water-soluble palladium compounds, whereas auric (III) chloride or tetra-chloroauric (III) acid and the alkali metal salts thereof can be used as the water-soluble gold compounds. The generally available tetrachloroauric (III) acid and the sodium palla-dium (II) chloride are preferred because of their high water solubility. Typically, the quantity of these compounds employed is such as to provide 1 to 10 grams of palladium and 0.5 to 5 grams of gold per liter of finished catalyst. Accordingly, the amount of gold present in the catalyst will be from about 10 to about 70% of the amount of palladium. Preparation of catalyst for the manufacture of vinyl acetate from ethylene, oxygen, and acetic acid according to the method of this invention can provide a catalyst with at least 17 wt % more palladium and at least 12 wt % more gold than by the use of the method of U.S. Pat. No. 5,332,710. The method of this invention can provide a catalyst with at least an equivalent amount or greater of gold than by the use of U.S. Pat. No. 5,314,858.

Comparative examples were performed on catalysts pre-pared by the method of this invention (separate fix technique) as described herein and the double fix technique prepared in accordance with U.S. Pat. No. 5,314,858. Table 2 illustrates the results of these examples. It can be seen that the method of this invention provided greater gold retention than the method of U.S. Pat. No. '858.

The volume of solution used for impregnating the support with the precious metals is important. For effective deposition, the volume of the impregnating solution should be from 95 to 100% of the absorptive capacity of the catalyst support and preferably it should be 98–99%.

The support material for the catalyst according to the present invention can be of any diverse geometrical shape. For example, the support can be shaped as spheres, tablets or cylinders. The geometrical dimensions of the support material can, in general, be in the range of 1–8 mm. A most suitable geometrical shape is, in particular, the spherical shape, for example, spheres with diameters in the range of 4–8 mm. These supports are generally called pills.

The specific surface area of the support material can vary within wide limits. For example, support materials which have an inner surface area of 50–300 $m^2/g$ and especially 100–200 $m^2/g$ (measured according to BET) are suitable.

Examples of support materials which can be used include silica, aluminum oxide, aluminum silicates or spinels. Silica is the preferred support material.

After each impregnation of the support with the water soluble palladium or gold compound, the impregnated sup-port may be dried prior to fixing the palladium or gold compound as a water insoluble compound on the support. The fixing solution is one which comprises an alkaline solution, for example, an aqueous solution which contains alkali metal hydroxides, alkali metal bicarbonates and/or alkali metal carbonates. It is particularly preferred to use aqueous solutions of sodium hydroxide or potassium hydroxide. By treatment with the alkaline solution, the precious metal salts are converted to water insoluble com-pounds believed to be hydroxides and/or oxides, at least in the case where the alkaline solution is a solution of sodium hydroxide or potassium hydroxide.

According to the prior art, the alkaline fixing solution was dispersed onto the impregnated supports and the treated supports were allowed to stand for up to 24 hours or more during the precipitation. The volume of fixing solution was that equal to the dry absorptivity of the support and the amount of alkaline compound used was in excess on a molar basis of that required to react with all of the impregnated precious metal salts.

For the method of the present invention, in each fixing step, the amount of the alkaline compound contained in the fixing solution should be such that the ratio of alkali metal to anion from the water soluble precious metal salt be from about 1:1 to about 1.8:1 molar.

The volume of solution in each fixing step can be equiva-lent to the pore volume of the support or the impregnated support can be fully immersed in the fixing solution wherein the total volume of solution is sufficient to cover the volume of the support. Alternatively, the support can be impregnated in one or both of the separate fixing steps by a process designated "rotation immersion" which is set forth in com-monly assigned application U.S. Pat. No. 5,332,710. In this process, the impregnated catalyst support is immersed in the alkaline fixing solution and tumbled or rotated therein at least during the initial steps of the precipitation of the water insoluble precious metal compounds. The rotation or tum-bling of the supports in the alkaline fixing solution should proceed for at least 0.5 hour upon the initial treatment and, preferably, for at least 2.5 hour. The rotation immersion treatment can last as long as up to 4 hours and the treated supports may be allowed to stand in the fixing solution to insure that complete precipitation of the water soluble precious metal compounds takes place.

Any type of rotation or tumbling equipment can be used as the exact apparatus utilized is not critical. What may be critical, however, is the extent of the rotating motion. Thus, the rotation should be sufficient so that all surfaces of the impregnated supports are evenly contacted with the alkaline fixing solution. The rotation should not be so harsh that actual abrasion of the insoluble precious metal compounds takes place such that the insoluble compounds are abraded off the support surface. Generally, the extent of rotation should be about 1 to 50 rpm and possibly even higher depending upon the exact support utilized and the amount of precious metal to be deposited on the support. The rpm to be used is variable and may also depend upon the apparatus utilized, the size and shape of the support, the type of support, metal loadings, etc., but should fall within the guidelines expressed above that while a small amount of abrasion may take place, it is not to be such that the insoluble compounds are actually abraded off the support surface to an unacceptable degree.

Prior to each fixing step the impregnated catalyst support may be dried to remove absorbed water. If fixing is carried out by the pore volume method, drying of the impregnated support is required to obtain fill contact of the precious metal with the fixing solution to cause precipitation. Preferably for the rotation immersion method the impregnated support is not dried prior to fixing.

Alternatively the impregnating solution containing the gold compound and the fixing solution can be mixed immediately prior to impregnation thus avoiding a separate fixing step. This is possible because the insoluble gold salt is quite slow to form at ambient room temperature.

Subsequent to the fixing, the supports are washed such as with distilled water so as to remove the anions, such as the chlorides, which are still contained on the support and freed from the initial impregnating solution. Washing is continued until all of the anions are removed from the support. Ideally no more than about 1,000 ppm of anion should remain on the catalyst. To ensure substantially complete removal of the anions such as chloride ion from the catalyst, the wash effluent can be tested with silver nitrate. The catalyst is then dried at temperatures not to exceed about 150° C.

The fixed and washed material is then treated with a reducing agent in order to convert the precious metal salts and compounds which are present into the metallic form. The reduction can be carried out in the liquid phase, for example, with aqueous hydrazine hydrate, or in the gas phase, for example, with hydrogen or hydrocarbons, for example, ethylene. If the reduction is carried out with a solution of hydrazine hydrate, the reaction is preferably carried out at normal temperature. When the reduction is carried out in the gas phase, it can be advantageous to carry out the reaction at elevated temperature, for example, at 100–200° C. in the case of reduction with ethylene. The reducing agent is appropriately employed in excess so that it is certain that all of the precious metal salts and compounds are converted into the metallic form.

Depending on the use for which the catalyst prepared in this way is intended, the latter can also be provided with customary additives. Thus, for example, additions of alkali metal acetates are advantageous when the catalyst is to be used for the preparation of unsaturated esters from olefins, oxygen and organic acids. In this case, for example, the catalyst can, for this purpose, be impregnated with an aqueous solution of potassium acetate and then dried.

The catalysts according to the invention can be used with particular advantage in the preparation of vinyl acetate from ethylene, oxygen and acetic acid in the gas phase. For this purpose, those catalysts according to the invention which contain silica as the support material and additives of alkali metal acetates are particularly suitable. In the above mentioned preparation of vinyl acetate, such catalyst are also distinguished by high activity and selectivity and by long life.

EXAMPLES 1–11

The catalysts of Examples 1–4 were prepared in accordance with the method of the present invention. The specific examples are described in Table 1. For each example, silica catalyst supports provided by Sud Chemie having a spherical shape and a diameter of about 7.3 mm were utilized unless otherwise specified. In all the examples, 250 cc of the supports were impregnated with an aqueous solution containing sufficient sodium palladium chloride to provide 1.65 g (6.6 g/l) palladium on the support. In Table 1 the term "incipient wetness" is known in the art to mean a volume of solution equal to the pore volume of the support. The treated supports were then fixed with an aqueous solution of sodium hydroxide according to the method described in Table 1. The amount of sodium hydroxide used in the first fixing step as defined as the molar ratio of sodium cation to chloride anion is 1.2:1. Variations in the fixing times are also set forth in Table 1. After the first fixing, the treated material was thoroughly washed with distilled water to remove the chloride ions. The water flow rate was about 200 cc/min for approximately 5 hours except where otherwise noted. After washing the catalysts were air dried for one hour at 100° C. The dried catalysts were then impregnated with 0.75 g (3.0 g/l) gold used as an aqueous solution of sodium chloroaurate. The treated supports were then fixed with an aqueous solution of sodium hydroxide according to the method described in Table 1. The amount of sodium hydroxide used in the second fixing step as defined as the molar ratio of sodium to chloride anion is 1.2:1. Variations in the fixing times are also set forth in Table 1. After the second fixing, the base treated material was thoroughly washed with distilled water to remove the chloride ions. The water flow rate was about 200 cc/min for approximately 5 hours unless otherwise noted. After washing the catalysts were air dried in a nitrogen atmosphere at 150° C. Each prepared catalyst was then reduced with ethylene gas at a temperature of 150° C. The reducing gas contained 5% ethylene in nitrogen and was passed over the catalysts for 5 hours at atmospheric pressure. The reduced catalyst was impregnated with an aqueous solution containing 10 grams (40 g/l) of potassium acetate at a solution volume equal to the support absorptivity. The catalysts were dried at a temperature no greater than 150° C.

The catalysts of examples 4–6 were prepared in accordance with the method described in U.S. Pat. No. 5,314,858. The catalysts of example 7–11 were prepared in accordance with the method of the present invention. Initial and final metal loadings are identified in Table 2. It can be seen that the average metal retention for Pd under the technique of U.S. Pat. No. '858 was 88%, and for Au was 77%, while the average metal retention for Pd under the inventive technique was 88%, and for Au was 85%. The catalysts of Examples 1–11 were utilized to prepare vinyl acetate by the reaction of ethylene, oxygen and acetic acid according to methods well known in the art.

TABLE 1

| METHOD | Run #1 | Run #2 | Run #3 | Run #4 |
|---|---|---|---|---|
| Pd Impreg. Drying | Incipient wetness no drying | Incipient wetness no drying | Incipient wetness no drying | Incipient wetness with drying at 100° C./1 hr |

TABLE 1-continued

| METHOD | Run #1 | Run #2 | Run #3 | Run #4 |
|---|---|---|---|---|
| Pd Fixing | Rotation immersion 2.5 hr 1.2:1Na/Cl | Rotation immersion 2.5 hr 1.2:1Na/Cl | Immersion 16 hr 1.2:1Na/Cl | Incipient wetness 16 hr 1.2:1Na/Cl |
| First Washing | 5 hr | 5 hr | 5 hr | 5 hr |
| First Drying | 100° C. 1 hr | 100° C. 1 hr | 100° C. 1 hr | 100° C. 1 hr |
| AU Impreg. Drying | Incipient wetness with drying at 100° C./1 hr | Impregnated and fixing solution mixed 16 hr no drying | Incipient wetness with drying at 100° C./1 hr | Incipient wetness with drying at 100° C./1 hr |
| Au Fixing | Incipient wetness 16 hr 1.2:1Na/Cl | N.A. | Incipient wetness 16 hr 1.2:1Na/Cl | Incipient wetness 16 hr 1.2:1Na/Cl |
| Second Washing | 5 hr | 11 hr | 5 hr | 5 hr |
| Second Drying | 150° C. in $N_2$ sweep 16 hr | 150° C. in $N_2$ sweep 16 hr | 150° C. in $N_2$ sweep 16 hr | 150° C. in $N_2$ sweep 16 hr |

TABLE 2

Comparative Examples
Employing The Present Method (Separate Fix)
and Double Fix Method Per U.S. Pat. No. 5,314,858

| Method | Example | Initial Loadings Au g/l | Initial Loadings Pd g/l | Final Loadings Au g/l | Final Loadings Pd g/l | Yields % Au | Yields % Pd |
|---|---|---|---|---|---|---|---|
| Double Fix | 4 | 3.30 | 7.00 | 2.58 | 6.05 | 78 | 86 |
| | 5 | 3.25 | 6.90 | 2.35 | 6.06 | 72 | 88 |
| | 6 | 3.45 | 7.31 | 2.77 | 6.57 | 80 | 90 |
| | | | | | AVERAGE | 77 | 88 |
| Separate Fix | 7 | 3.73 | 7.00 | 3.14 | 6.10 | 84 | 87 |
| | 8 | 3.73 | 7.00 | 3.25 | 5.91 | 87 | 84 |
| | 9 | 4.00 | 7.00 | 3.28 | 6.02 | 82 | 86 |
| | 10 | 4.30 | 7.50 | 3.75 | 6.76 | 87 | 90 |
| | 11 | 4.00 | 7.00 | 3.47 | 6.42 | 87 | 92. |
| | | | | | AVERAGE | 85 | 88 |

What is claimed is:

1. In a method of preparing a catalyst composed of a porous support containing thereon palladium and gold metals comprising; impregnating said support with water soluble compounds of such precious metals, converting said absorbed water soluble precious metal compounds to water insoluble precious metal compounds by contacting the impregnated support in a fixing step with a solution containing a compound reactive with said water soluble precious metal compounds to precipitate on said support water insoluble precious metal compounds and reducing said water insoluble precious metal compounds with a reducing gas to form free precious metals on said support, the improvement which consists in (1) contacting said supports with one of said water soluble compounds of said precious metal to impregnate the water soluble compound on the support (2) converting said water soluble precious metal compound to water insoluble precious metal compound by contacting said impregnated support in a first fixing step with a solution containing a compound reactive with said water soluble compound to precipitate on said support said water insoluble precious metal compound (3) contacting said first impregnated and fixed support with the second of said water soluble compounds of said precious metal to impregnate the water soluble compound on the support (4) converting said second water soluble compounds of said precious metals to water insoluble precious metal compound by contacting said impregnated support in a second fixing step with a second solution containing a compound reactive with said second water soluble compound to precipitate on said support said second water insoluble precious metal compound, and thereafter reducing said water insoluble precious metal compounds to form free precious metals on said support.

2. The method of claim 1 wherein the reactive compound in each first and second fixing step is an alkaline compound.

3. The method of claim 2 wherein said alkaline compound comprises potassium or sodium hydroxide.

4. The method of claim 1 wherein the volume of said reactive solution contacted with said impregnated support in the said first fixing step is equal to the dry absorptivity of said support.

5. The method of claim 1 wherein the volume of said solution contacting said impregnated support in said first fixing step is sufficient to immerse the support.

6. The method of claim 1 wherein the volume of said reactive solution contacted with said impregnated support in the said second fixing step is equal to the dry absorptivity of said support.

7. The method of claim 1 wherein the volume of said reactive solution contacted with said impregnated support in said second fixing step is sufficient to immerse the support.

8. The method of claim 5 wherein the said first fixing step is carried out by the rotation immersion method.

9. The method of claim 8 wherein the precious metal first contacted with the support and subjected to the first fixing step is Pd.

10. A method of preparing a catalyst comprising
   (1) contacting a solution of water soluble Pd with a porous support to impregnate the water soluble Pd on the support;
   (2) converting said water soluble Pd metal compound to water insoluble Pd compound by contacting the Pd compound and support in a first fixing step with an alkaline compound wherein the support is immersed in the alkaline compound and tumbled at least during the initial steps of the precipitation of the water insoluble Pd compound;
   (3) contacting the first impregnated and fixed support with water soluble Au metal compound to impregnate the water soluble Au on the support;
   (4) converting said water soluble Au metal compound to water insoluble Au compound by contacting the Au compound and support in a second fixing step with an alkaline compound wherein the support and alkaline compound are contacted by incipient wetness; and, (5) reducing the Pd and Au metal compounds with a reducing agent to form free Pd and Au metals on the support.

11. A method of preparing a catalyst comprising (1) contacting a solution of water soluble Pd with a porous support to impregnate the water soluble Pd on the support;

(2) converting said water soluble Pd metal compound to water insoluble Pd compound by contacting the Pd compound and support in a first fixing step with an alkaline compound wherein the support is immersed in the alkaline compound and tumbled at least during the initial steps of the precipitation of the water insoluble Pd compound;

(3) contacting the first impregnated and fixed support with water soluble Au metal compound and an alkaline compound so as to impregnate the water soluble Au on the support and simultaneously performing a second fixing step; and (4) reducing the Pd and Au metal compounds with a reducing agent to form free Pd and Au metals on the support.

* * * * *